United States Patent
Whitt et al.

(10) Patent No.: US 6,309,359 B1
(45) Date of Patent: Oct. 30, 2001

(54) METHOD AND APPARATUS FOR NONINVASIVE DETERMINATION OF PERIPHERAL ARTERIAL LUMENAL AREA

(76) Inventors: Michael D. Whitt, 23348 Via Sausalito, Moreno Valley, CA (US) 92557; Gary M. Drzewiecki, 12 Park La., Princeton, NJ (US) 08540; James J. Pilla, 110 Knoxlyn Farm Dr., Kennett Square, PA (US) 19348

( * ) Notice: Subject to any disclaimer, the term of this patent is extended or adjusted under 35 U.S.C. 154(b) by 0 days.

(21) Appl. No.: 09/205,042

(22) Filed: Dec. 3, 1998

Related U.S. Application Data

(60) Provisional application No. 60/087,515, filed on Jun. 1, 1998.

(51) Int. Cl.[7] .................................................. A61B 5/02
(52) U.S. Cl. ........................... 600/507; 600/485; 600/492; 600/495; 600/499; 600/504
(58) Field of Search ..................................... 600/485, 481, 600/490, 492, 493–496, 500, 507, 526, 499, 504

(56) References Cited

U.S. PATENT DOCUMENTS

| | | | |
|---|---|---|---|
| 5,103,833 | 4/1992 | Apple | 128/687 |
| 5,724,981 | * 3/1998 | Apple | 600/493 |

* cited by examiner

*Primary Examiner*—Cary O'Connor
*Assistant Examiner*—Ryan Carter
(74) *Attorney, Agent, or Firm*—Skjerven Morrill MacPherson LLP

(57) ABSTRACT

An occlusive cuff is placed around a limb (e.g. an arm) of a patient. A fluid, such as air, is pumped into the cuff, and the pressure in the cuff is measured. The pressure variation in the cuff with respect to time is caused by the pump and expansion/contraction of the arm caused by blood being pumped therethrough by the patient's heart. This variation in pressure is used to calculate systolic and diastolic pressure, artery lumen area compliance and artery volume compliance, artery lumen area, and the blood flow rate through the patient's arteries (e.g. the brachial artery for the case of the patient's arm, or the femoral artery or the case of the patient's leg).

14 Claims, 15 Drawing Sheets

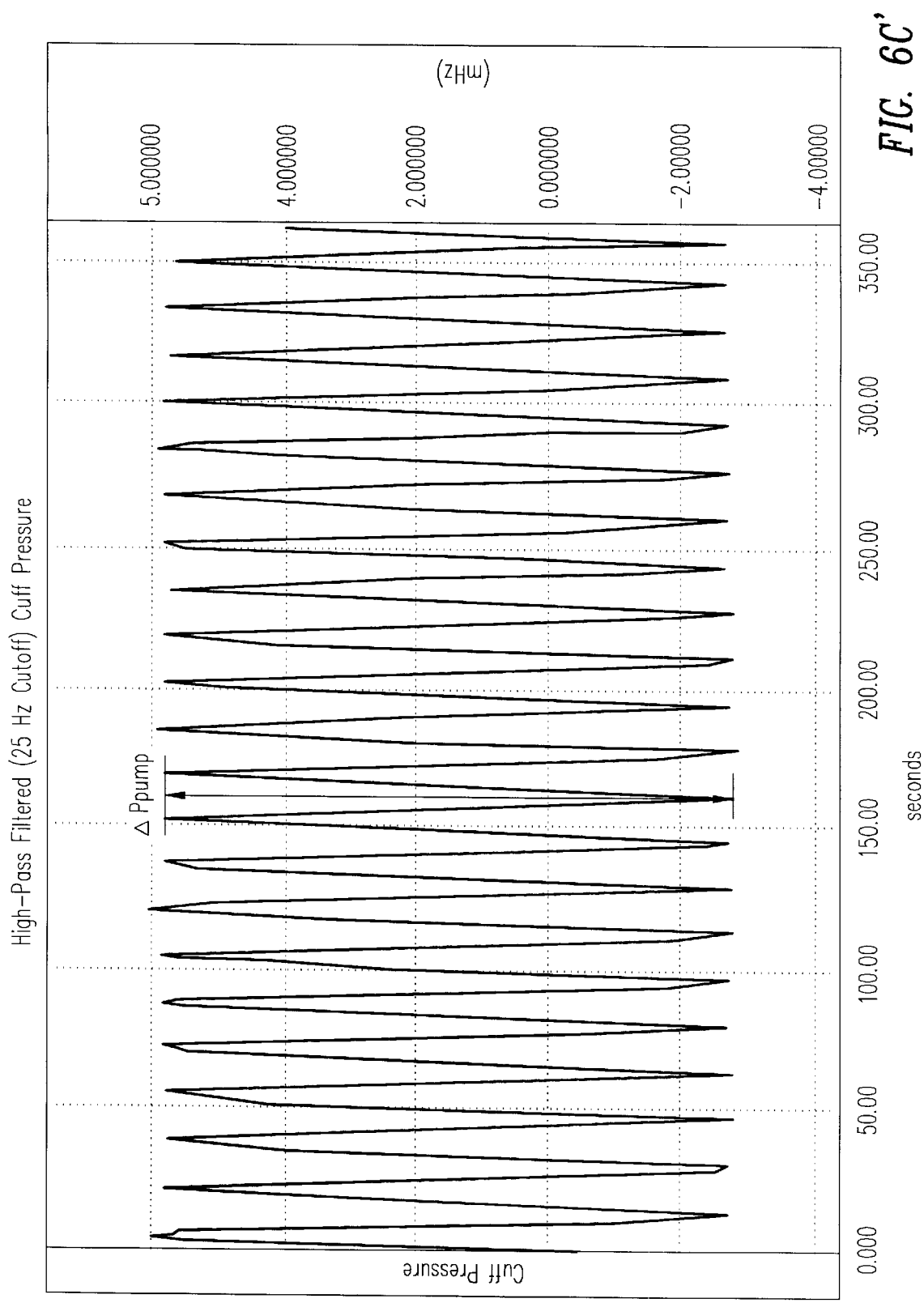

US 6,309,359 B1

METHOD AND APPARATUS FOR NONINVASIVE DETERMINATION OF PERIPHERAL ARTERIAL LUMENAL AREA

CROSS-REFERENCE TO RELATED APPLICATIONS

This patent claims priority based on provisional U.S. patent application Ser. No. 60/087,515, filed Jun. 1, 1998.

BACKGROUND OF THE INVENTION

This invention pertains to a non-invasive apparatus and method for measuring arterial compliance, arterial lumen area, the amount of blood flowing through the artery, and the phase lag between the pressure and blood flow waveforms.

Occlusive cuffs are commonly used to measure blood pressure using the auscultatory method. During this method, the cuff is placed on a patient's arm, inflated, and gradually deflated while the attending physician relies on the generation of Korotkoff sounds to determine systolic and diastolic pressure. It is known in the art, however, that occlusive cuffs can be used in other ways to obtain other valuable information.

Measuring Changes in the Volume of an Artery with an Occlusive Cuff

Windsor, "The Segmental Plethysmograph," Angiology, Vol. 8, p. 87, 1957, discusses using an occlusive cuff to measure variations in the size of a limb (e.g. an arm). Windsor is incorporated herein by reference. FIG. 1 illustrates Windsor's apparatus, known as a plethysmograph, which includes an occlusive cuff 10, a bulb 12 for pumping air into Windsor's apparatus, a valve 14 for isolating the apparatus from bulb 12, and a differential pressure chamber 16 comprising a diaphragm 18. As the volume of a patient's arm varies (e.g. because of blood pumped through the arm by the patient's heart) this variation in volume $\Delta V$ can be measured with Windsor's apparatus using the equation $$Ad = K\Delta V$$

where A is the area of diaphragm 18, d is the displacement of diaphragm 18, and K is a proportionality constant.

$$K = V_0/(V_0 + V_1)$$

where $V_0$ is the original volume of an inactive portion 20 of Windsor's system, and $V_1$ is the original volume of an active portion 22 of the system.

Measuring Systolic and Diastolic Pressure with an Occlusive Cuff

It is known in the art that one can use an occlusive cuff to measure a patient's systolic and diastolic pressure using the "oscillometric method," e.g. as described by Drzewiecki, et al., "Theory of the Oscillometric and the Systolic and Diastolic Detection Ratios," Annals of Biomedical Engineering, Vol. 22, pp. 88–96 (1994), incorporated herein by reference. During this method, an occlusive cuff is placed on a patient's arm, inflated, and slowly deflated while the cuff pressure is monitored. FIG. 2A illustrates cuff pressure vs. time during this method. A portion 30 of FIG. 2A illustrates pressure while the cuff is being inflated, and a portion 32 illustrates pressure while the cuff is being deflated. As can be seen, there is a set of small ridges and valleys in the waveform of FIG. 2A. These ridges and valleys are caused by the expansion and contraction of the patient's brachial artery that occur when the patient's heart pumps blood through the artery.

FIG. 2B shows the waveform of FIG. 2A after it has been band-pass filtered to isolate the portion of the signal between 0.5 and 5 Hz and amplified. This permits isolation and observation of the portion of cuff pressure oscillation caused by the artery expanding and contracting. As can be seen, the amplitude of the pulses gradually increases, reaches a maximum, and then decreases as the cuff deflates. The pulses of FIG. 2B are at their maximum amplitude when the cuff pressure equals the mean arterial pressure ("MAP"). One can calculate the systolic pressure as that pressure, above the MAP, at which the oscillation pulses have an amplitude As such that:

$$As/Am = 0.55$$

where Am is the maximum pulse amplitude (which, as mentioned above, occurs when the cuff is at the MAP). In other words, the cuff pressure (above the MAP) which produces pulse amplitudes that equal 55% of the pulse amplitude at the MAP equals the systolic pressure.

The diastolic pressure equals that cuff pressure (below the MAP) which produces pulses having an amplitude Ad such that:

$$Ad/Am = 0.85$$

In other words, the cuff pressure (below the MAP) that produces pulse amplitudes that equal 85% of the pulse amplitude at the MAP equals the diastolic pressure.

Using an Occlusive Cuff to Measure Artery Lumen Size

Cuff pressure exerts a radial force on the brachial artery directed towards the center of the lumen of the artery As the cuff pressure decreases, the magnitude of the force acting on the artery directed toward the center of the lumen of the artery decreases. Also, as the cuff pressure increases, the magnitude of the force acting on the artery directed toward the center of the lumen of the artery increases. The difference between blood pressure and cuff pressure is called the "transmural pressure". The brachial artery exhibits compliance (i.e., elasticity) which differs with transmural pressure. As the cuff pressure decreases transmural pressure increases. Thus, the artery lumen size increases as the transmural pressure increases.

If the cuff pressure exceeds the blood pressure in the brachial artery, the artery lumen contracts. At sufficiently high pressure (e.g. more than 200 mm Hg), the brachial artery is pinched closed, and the lumen area is effectively zero. FIG. 3 illustrates the relation between an artery lumen area and the transmural pressure. FIG. 4 illustrates the artery compliance (e.g., elasticity) with respect to pressure. As can be seen, the artery is most compliant when the transmural pressure is zero (i.e., when the blood pressure in the artery equals cuff pressure). At very low transmural pressures and high transmural pressures, artery compliance drops.

Pilla, "Calibrated Cuff Plethysmography: Development and Application of a Device For Use in Evaluation of the Effect of Arterial Pressure-Volume Curve Alterations on Systemic Blood Pressure," PhD. Dissertation, Rutgers University (May, 1995) discusses using an occlusive cuff to determine the pressure versus lumen area characteristics of a patient's brachial artery. Pilla is incorporated herein by reference. FIG. 5 schematically illustrates Pilla's apparatus 50. As shown in FIG. 5, apparatus 50 includes an occlusive cuff 52 to be placed around a patient's arm (not shown), a pump 54 for pumping air into cuff 52, a pair of valves 56, 58, a pressure transducer 60, and an electrical circuit 62 for amplifying the signal provided by transducer 60.

As explained below, Pilla uses pump 54 and transducer 60 to approximate the change in cuff volume caused by a change in pressure within cuff 52 (i.e., cuff compliance). Pilla then uses this approximation of the cuff compliance and the pressure measured by transducer 60 to calculate the change in the patient's arm diameter (e.g., caused by expansion and contraction of the brachial artery) caused by the patient's pulse.

Pilla begins his process by passing water through pump 54 to determine the stroke volume of the pump. This information is used in subsequent calculations of cuff compliance.

Pilla then places valve 56 in a first position such that air from the atmosphere flows into an input conduit 54a of pump 54, and air from an output conduit 54b of pump 54 flows into cuff 52 to thereby inflate cuff 52. After cuff 52 is inflated to a pressure in excess of the patient's systolic pressure, valve 56 is adjusted so that pump 54 removes air from cuff 52 and pumps air back into cuff 52 (e.g. as indicated by arrow A). Because of the manner in which valves 56 and 58 are adjusted, pump 54 cooperates with cuff 52 to superimpose a sinusoidal pressure variation on the air in cuff 52.

Transducer 60 measures the pressure in cuff 52 The pressure in cuff 52 varies in response to two things:

a) air being pumped in and out of cuff 52 by pump 54; and b) the expansion and contraction of the patient's arm caused by the patient's heart pumping blood through the arm. (This change in arm size is mostly due to expansion and contraction of the patient's brachial artery.)

Pilla's pump has a stroke frequency of 50 to 60 Hz. The patient's heart beats at a frequency between 0.5 and 1 Hz. Pilla passes the output signal from circuit 62 to a high pass filter 63 and a low pass filter 64. High pass filter 63 passes signals having a frequency greater than 25 Hz, whereas low pass filter 64 passes signals having a frequency less than 25 Hz. Therefore, filter 63 provides an indication of the cuff pressure variation caused by pump 54, whereas filter 64 provides an indication of the cuff pressure variation caused by the patient's heart beating.

Pilla periodically removes air from cuff 52 via valve 58. The waveform of pressure vs. time provided by transducer 60 and circuit 62 is shown in FIG. 6. The step-like nature of the FIG. 6 waveform is caused by the periodic reduction in cuff pressure caused by periodically opening valve 58. FIG. 6A shows an amplified portion of the FIG. 6 output signal. Low pass filter 64 receives this signal and generates in response thereto the signal shown in FIG. 6B, which represents that portion of the waveform caused by the patient's pulse. Similarly, high pass filter 63 receives the signal of FIG. 6 and generates in response thereto the signal of FIG. 6C, which represents the portion of the signal caused by pump 54. (An amplified version of this signal is shown in FIG. 6C'.) Pilla uses the output signal from high pass filter 63 to approximate the cuff compliance (i.e., the change in cuff volume caused by a change in cuff pressure). He uses the output of low pass filter 64 to determine the change in cuff pressure caused by the patient's pulse, and the previously approximated compliance value to calculate the change in cuff volume associated with the change in cuff pressure which is caused by the patient's pulse. This data is used to calculate arterial compliance and lumen area.

One of the objects of our invention is to provide a method for determining the arterial compliance and lumen area using an occlusive cuff with improved accuracy.

Another object of our invention is to provide a technique for continuously and accurately determining compliance of an occlusive cuff, and use the compliance to calculate arterial compliance and lumen size.

Another object of our invention is to use a high frequency calibration pump and flow meter to accurately determine cuff compliance.

Another object of our invention is to provide an improved method for determining artery area compliance from artery volume compliance.

Another object of the invention is to use an occlusive cuff to obtain additional data such as the phase lag between the arterial blood flow volume pulses and arterial pressure pulses.

SUMMARY

A method in accordance with our invention uses an occlusive cuff to provide systolic and diastolic pressure, artery lumen compliance, artery cross section area, and blood flow in a non-invasive manner. In accordance with our invention, a cuff is placed around a patient's arm and inflated. A pump periodically pumps a fluid in and out of the cuff, and the pressure in the cuff is measured. The cuff pressure vs. time waveform is passed through a low pass filter to provide a first portion of the pressure vs. time waveform which is caused by the patient's pulse. The pressure vs. time waveform is passed through a high pass filter to provide a second portion of the pressure vs. time waveform which is caused by the pump strokes.

Concurrently, a flow meter measures the volume of fluid pumped into and out of the cuff. The second portion of the pressure vs. time waveform and data from the flow meter are used to accurately calculate cuff compliance. The cuff compliance and the first portion of the pressure vs. time waveform are used to calculate the change in artery volume caused by the patient's pulse (i.e. the artery volume compliance).

The artery volume compliance is then used to determine the artery area compliance. One might assume that volume compliance equals area compliance times cuff length. However, because of certain "edge effects" involving a decreased transmission of pressure from the cuff to the artery at the ends of the cuff, volume compliance does not exactly equal area compliance times cuff length. Thus, in one embodiment, we determine a "correction factor" to account for these edge effects. This correction factor can be determined by using the cuff on a test subject and measuring the test subject's actual artery lumen area by magnetic resonance imaging. This correction factor is used to calculate the artery area compliance during subsequent measurements taken with the cuff. The correction factor enhances the accuracy of the determination of artery area compliance.

The artery area compliance is integrated to calculate the area of the artery lumen. The artery volume compliance is integrated to measure the volume of a segment of the artery.

The derivative of artery lumen volume with respect to time is multiplied by the artery compliance to calculate blood flow through the artery.

The phase lag between arterial pressure and blood flow is also determined.

In this way, the above-mentioned parameters are non-invasively determined with an occlusive cuff. These parameters are important for diagnosis of hypertension, direct diagnosis of peripheral arterial conditions, and diagnosis of coronary arterial conditions based on the correlation between the peripheral and coronary artery conditions.

BRIEF DESCRIPTION OF THE DRAWINGS

FIG. 6C' illustrates an amplified version of the signal of FIG. 6C.

DETAILED DESCRIPTION

Figure 7:
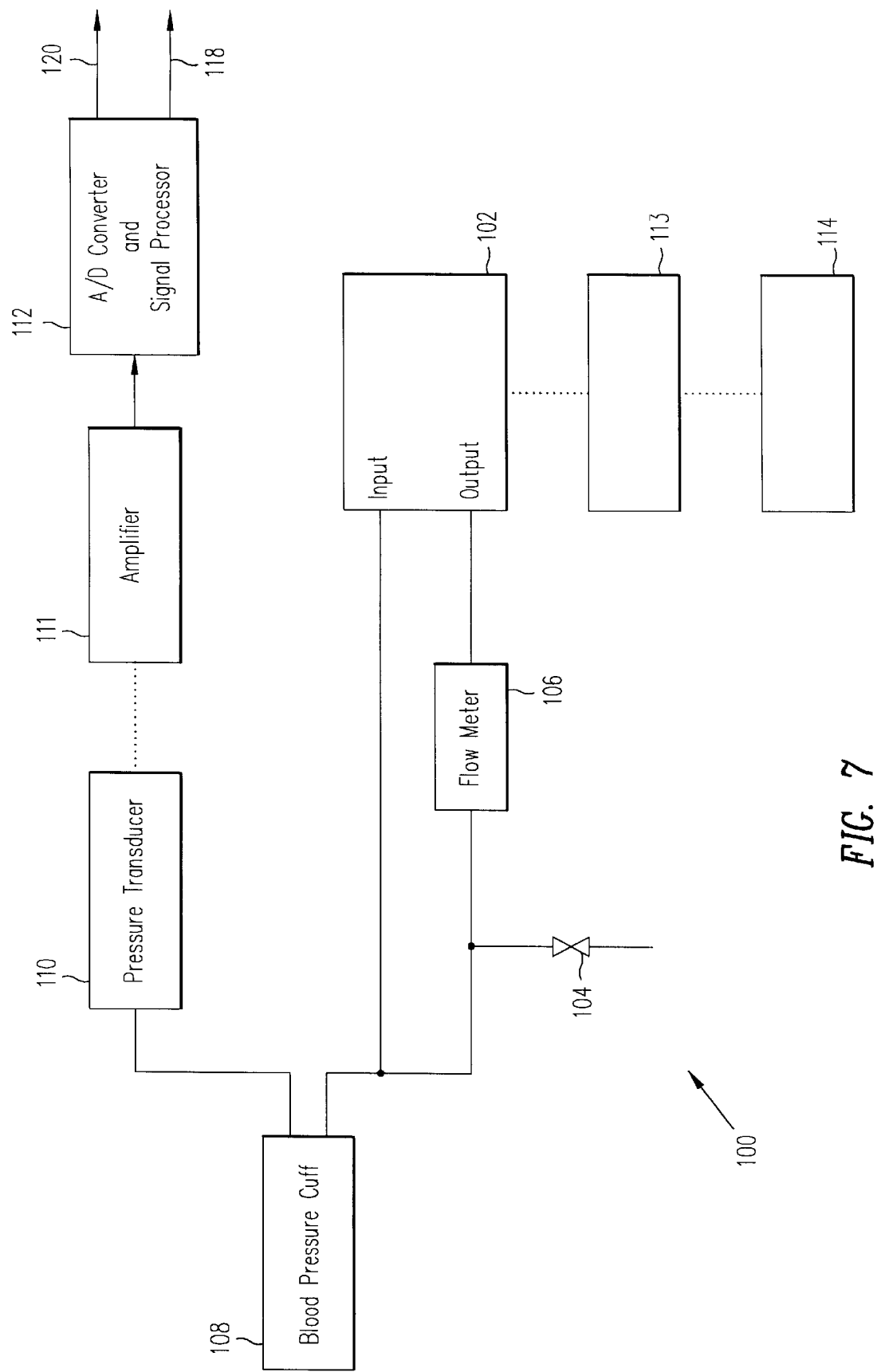
FIG. 7 schematically illustrates apparatus in accordance with our invention for measuring changes in volume in a patient's limb caused by the patient's pulse.

Referring to FIG. 7, apparatus 100 in accordance with our invention comprises a pump 102, a needle valve 104, a flow meter 106, a blood pressure cuff 108, and a pressure transducer 110. In one embodiment, pump 102 is a diaphragm pump with a flat line pump curve from 0 to 5 psig. In other words, pump 102 provides a constant known volume of gas per pump stroke over the relevant pressure range. (The fact that pump 102 is a flat line pump helps improve accuracy of our method.) In one embodiment, pump 102 is model number 5002, manufactured by ASF Incorporated of Georgia, flowmeter 106 is model No. KFG-3007, available from Kobold, and transducer 110 is model number TSD104 available from Biopak Corp. of California. The output signal from transducer 110 is connected to an electronic amplifier 111 (typically model DA100, manufactured by Biopak), which in turn is connected to A/D converter and signal processing circuit 112.

A motor speed control circuit 113 (typically device model no. 65DDC20-12, manufactured by Dart Controls, Inc.) controls the frequency of pump 102. In one embodiment, the frequency of pump 102 is set to be between about 20 to 30 Hz. However, other pump frequencies can be used. A power supply 114 (typically device no. 1HC12-3.4, manufactured by International Power, Inc.) provides power to motor speed control circuit 113.

One typically begins the process by ascertaining the stroke volume of pump 102. This can be done by measuring the volume of a fluid (e.g. a gas such as air) pumped by pump 102 over a period of time (e.g. ten seconds) divided by the number of strokes during that period of time. The fluid used to ascertain the stroke volume of pump 102 is typically the same fluid as that used to inflate cuff 108 during use of the cuff. This process can take place simultaneously with data acquisition and is monitored throughout the data acquisition procedure by using the flowmeter (106) and monitoring the signal received at the pressure transducer (110). The apparatus is then operated as follows. First, the cuff is placed around a patient's arm. Then, a bulb (not shown) is used to inflate cuff 108 above the patient's systolic pressure. In one embodiment, cuff 108 is inflated to about 180 mm Hg of pressure. Pump 102 is then used to pump air in and out of cuff 108. Valve 104 is actuated to gradually reduce pressure in cuff 108. While this is happening, transducer 110 measures the pressure in cuff 108 and flow meter 106 measures the volume of air (e.g. in liters/minute) provided by pump 102.

Figure 8:
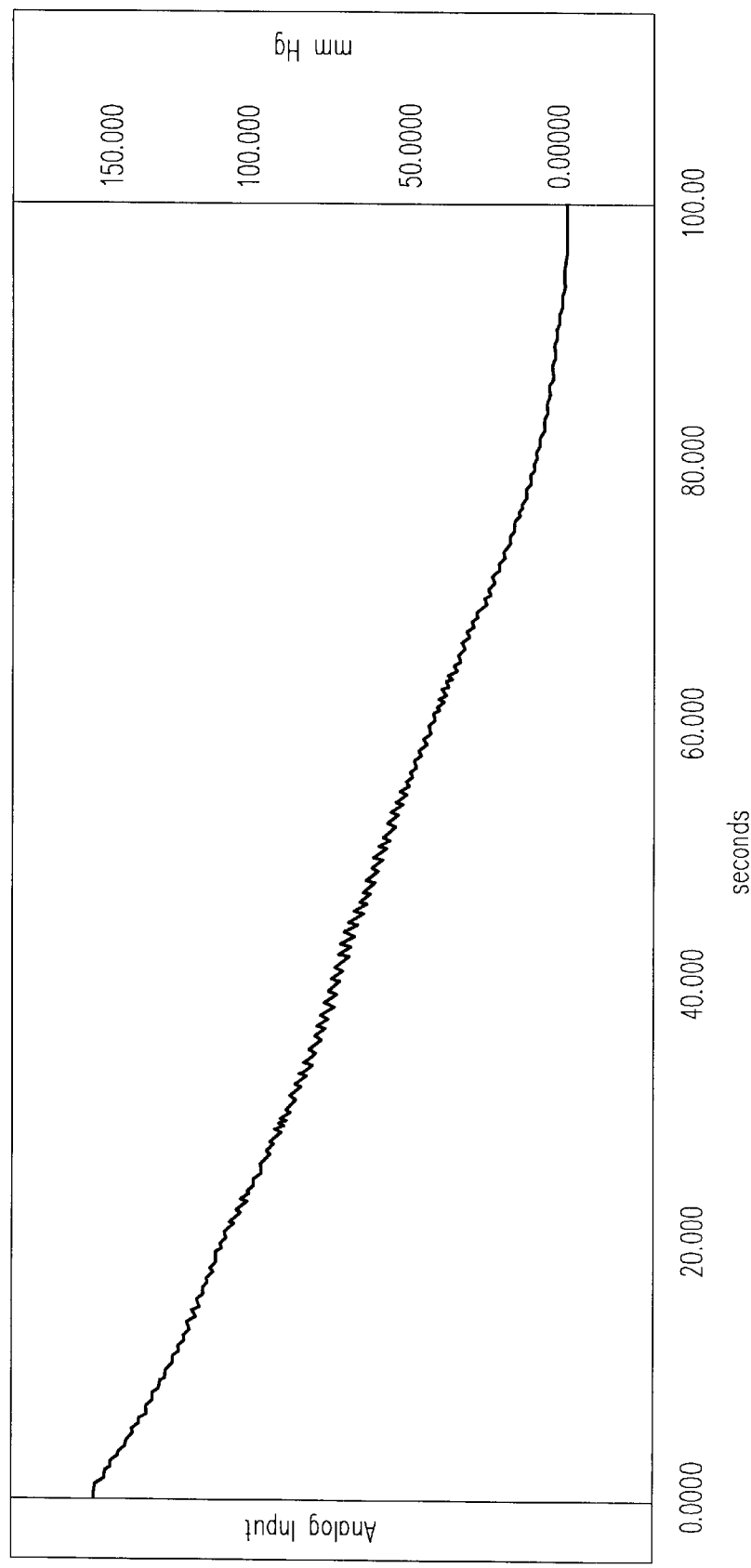
FIG. 8 illustrates the waveform produced by the transducer in the apparatus of FIG. 7 representing cuff pressure v. time.

The output signal provided by transducer 106 (shown in FIG. 8) includes:

1) a first component caused by air being pumped into and out of cuff 108 by pump 102; and 2) a second component caused by the patient's heart beating.

Figure 8A:
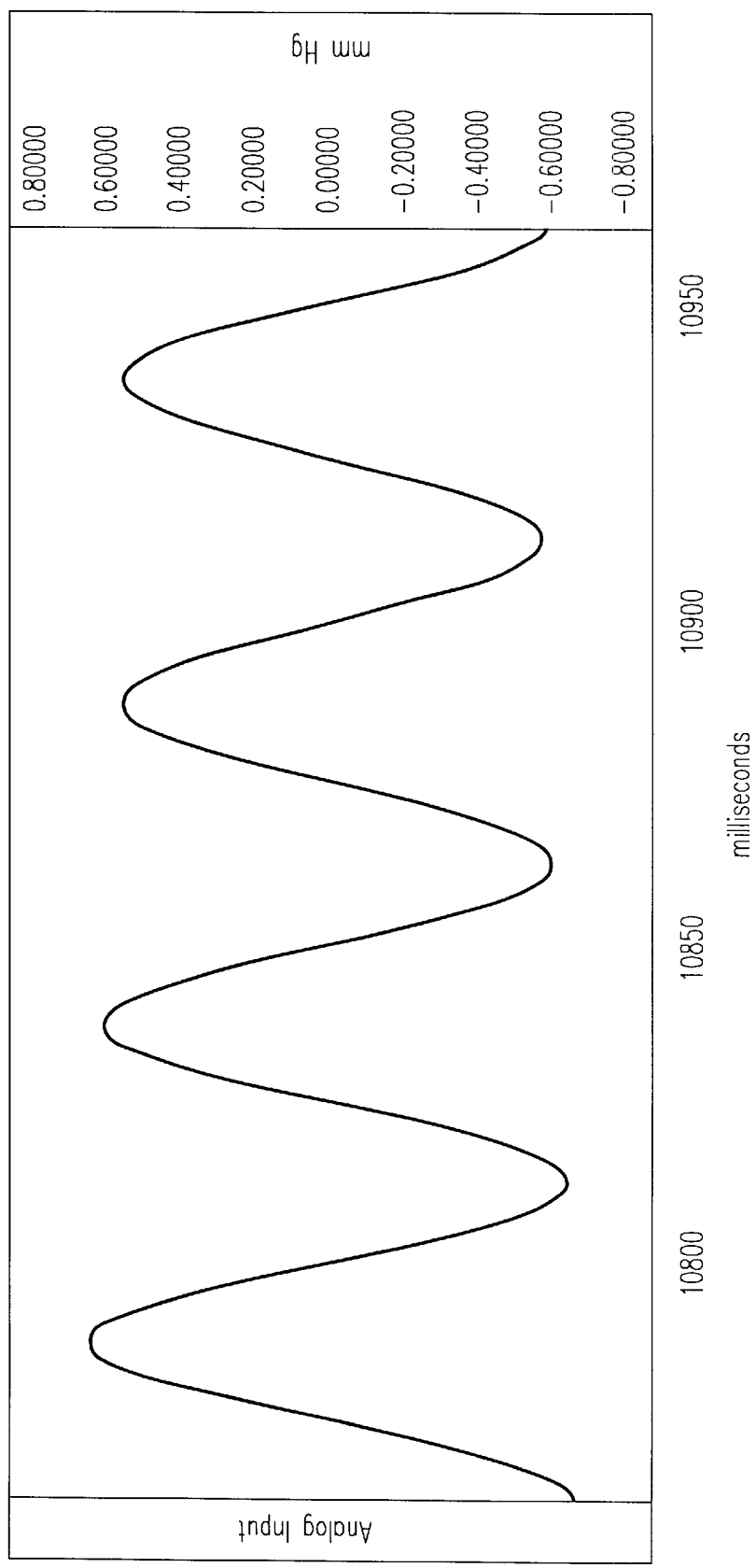
FIG. 8A illustrates that portion of the FIG. 8 waveform that is passed by a high pass filter (15 to 25 Hz).

The first component is separately analyzed by passing the signal from transducer 110 through a high band pass filter. For example, in an embodiment in which pump 102 has a stroke rate of 20 Hz, the signal from transducer 110 is passed through a high band pass filter which passes signals between 15 and 25 Hz. FIG. 8A illustrates an output signal 118 from the high band pass filter. The signal of FIG. 8A is essentially sinusoidal, with a frequency equal to the pump stroke rate.

Figure 8B:
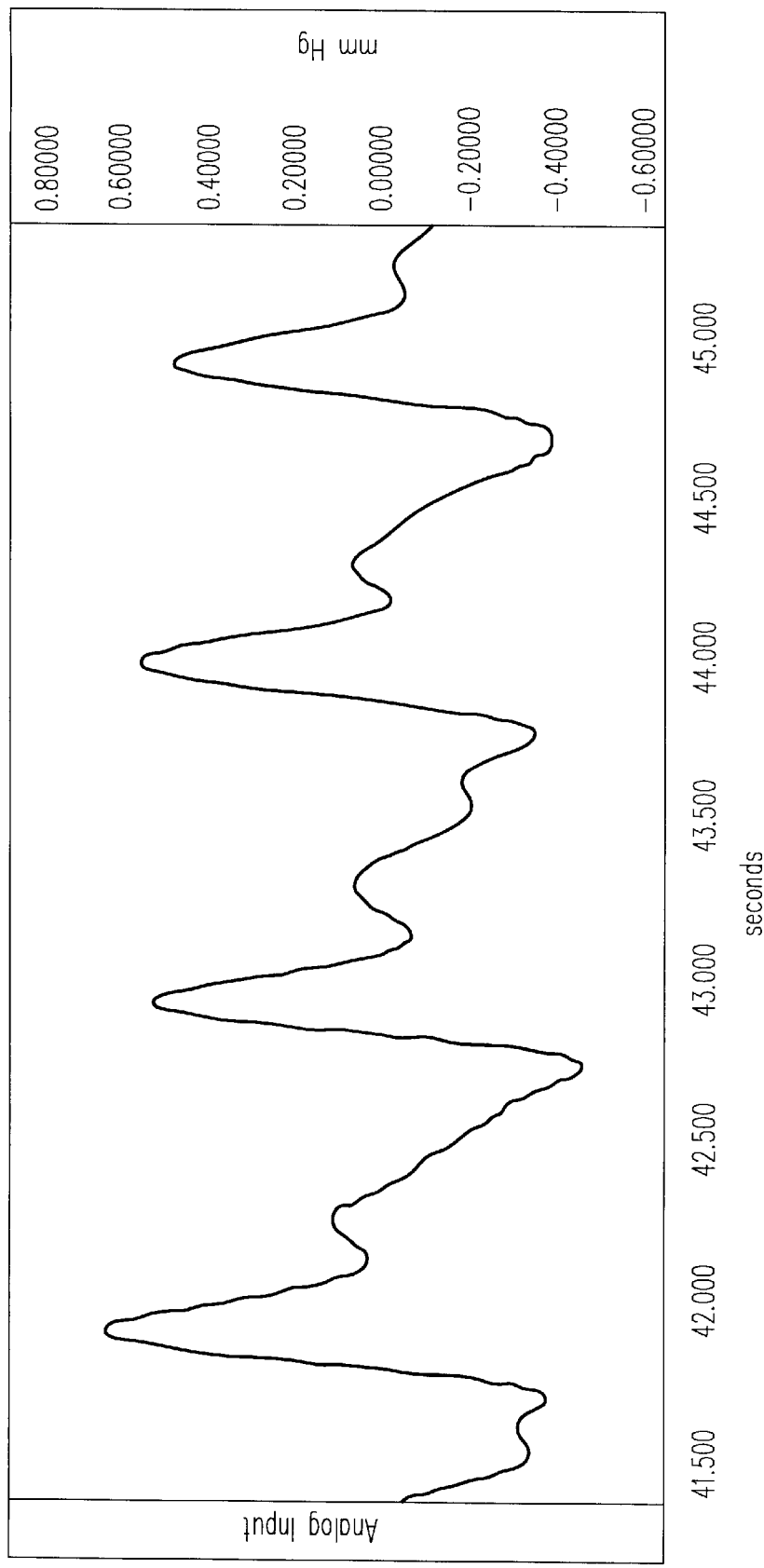
FIG. 8B illustrates that portion of the FIG. 8 waveform that is passed by a low pass filter (0.5 to 5 Hz).

The second component is separately analyzed by passing the signal from transducer 110 through a low pass filter that passes signals having frequencies between 0.5 and 5 Hz, thereby generating an output signal 120. Output signal 120 of the low pass filter is shown in FIG. 8B. (The reason for the 0.5 Hz cutoff is to eliminate that portion of the pressure vs. time waveform caused by slightly opening valve 104.) Signals 118 and 120 can be provided with either digital or analog filtering techniques.

These waveforms, along with data from flow meter 106 and the frequency of pump 102, are used to calculate the following parameters:

1. Systolic and diastolic pressure;
2. Arterial compliance;
3. Volume of blood flow through the artery per unit time;
4. Phase lag between the pressure and blood flow waveforms;
5. Arterial lumenal area; and
6. Cuff compliance.

Systolic and Diastolic Pressure

One obtains the systolic and diastolic pressures using the technique described below, i.e.:

1. Observing the size of the pulses of signal 120 to locate the cuff pressure corresponding to the maximum pulse size (which is the MAP).

2. Determining the cuff pressure above the MAP at which the pulses of signal 120 are 55% of their maximum value (their maximum value occurs when the cuff is at the MAP). This pressure is the systolic pressure.

3. Determining the cuff pressure below the MAP at which pulses of signal 120 are 85% of their maximum value. This pressure is the diastolic pressure.

Cuff Compliance

In order to perform the remaining calculations, one determines the relation between cuff volume pulsations and cuff pressure pulsations caused by pump 102. Occlusive cuffs stretch as pressure increases. This phenomenon is discussed by Drzewiecki, et al. in "Mechanics of the Occlusive Arm Cuff and Its Application as a Volume Sensor," IEEE Trans. Biomedical Engineering, Vol. 40, No. 7, July 1993, incorporated herein by reference. Thus, during a method in accordance with our invention, one calculates cuff compliance (referred to herein as $(dV/dP)_{pump\ at\ cuff}$) for each cuff pressure. This is calculated as follows 1. The difference in cuff volume caused by each pump stroke ($dV_{pump}$) is a known, constant value, measured by flow meter 106. In one embodiment, this can be determined since the flow rate (in volume/unit time) is measured by flow meter 106, and the stroke frequency of pump 102 is known. Flow rate divided by stroke frequency is the pump stroke volume.

2. The difference in cuff pressure caused by each pump stroke equals the amplitude of signal 118 from the high pass filter.

3. Cuff compliance $(dV/dP)_{cuff}$ equals $dV_{pump}$ divided by the amplitude of signal 118.

(Of importance, by using flow meter 106 and using actual measured pump volumes in this calculation, we continuously provide a more accurate measure of instantaneous cuff compliance than in the above-described Pilla method.)

As will be described below, once one determines the relation between cuff volume changes and cuff pressure changes, one uses this information to determine the change in cuff volume caused by the changes in cuff pressure due to the patient's pulse.

Calculation of Arterial Volume Compliance and Area Compliance

Figure 1:
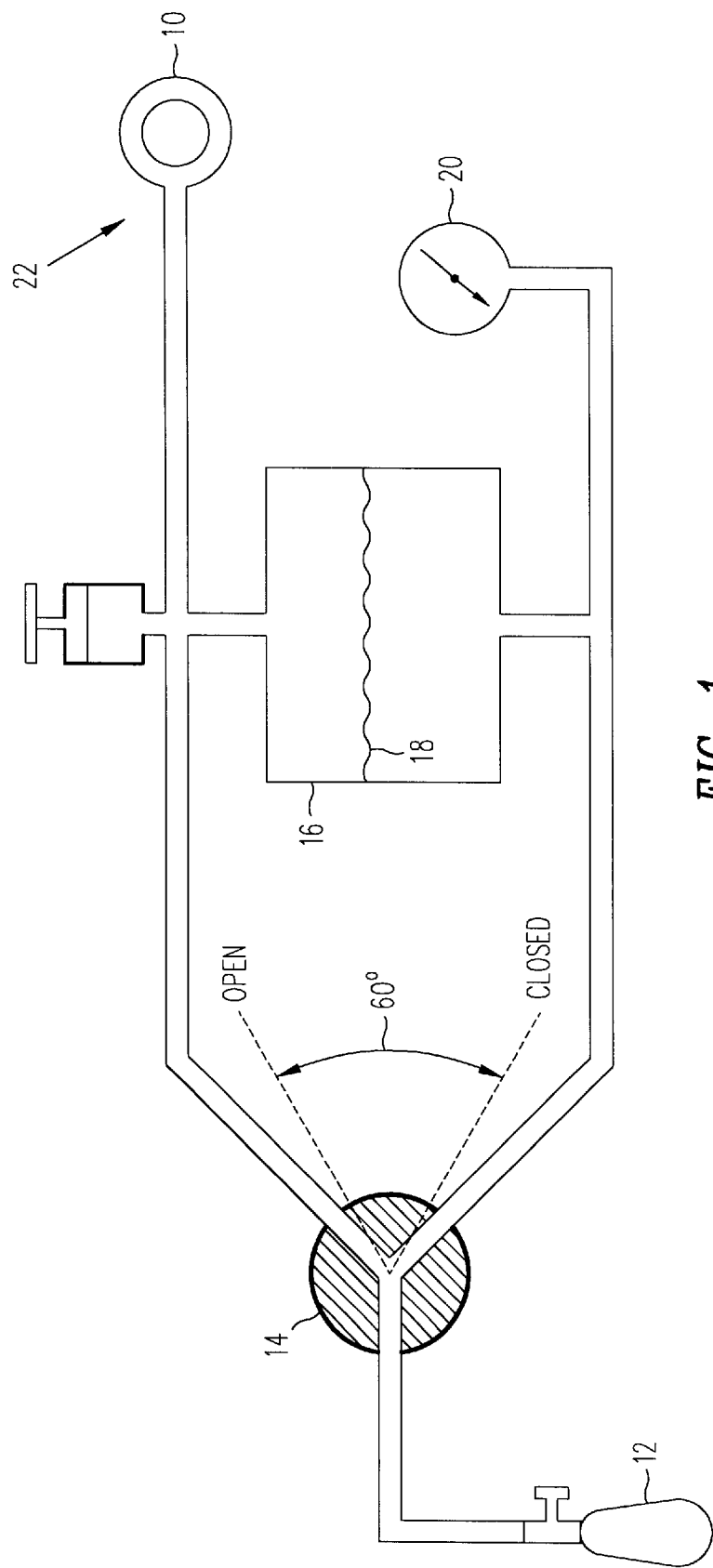
FIG. 1 schematically illustrates a segmental plethysmograph constructed in accordance with the prior art.
Figure 2A:
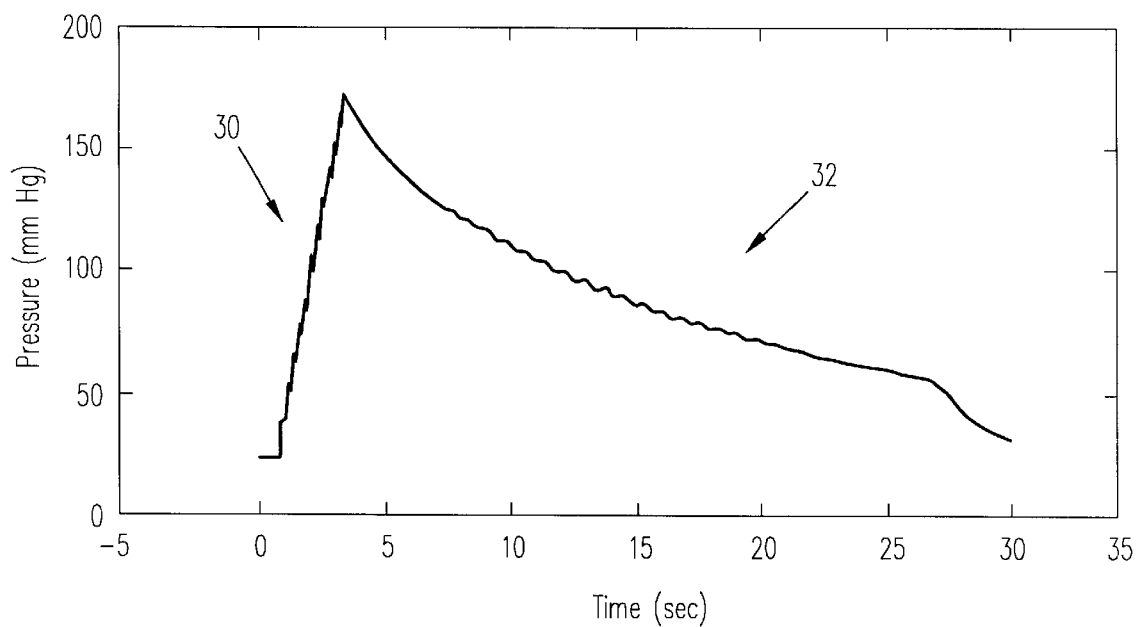
FIG. 2A illustrates cuff pressure versus time when an occlusive cuff is placed on a patient's arm, inflated, and then slowly deflated.
Figure 2B:
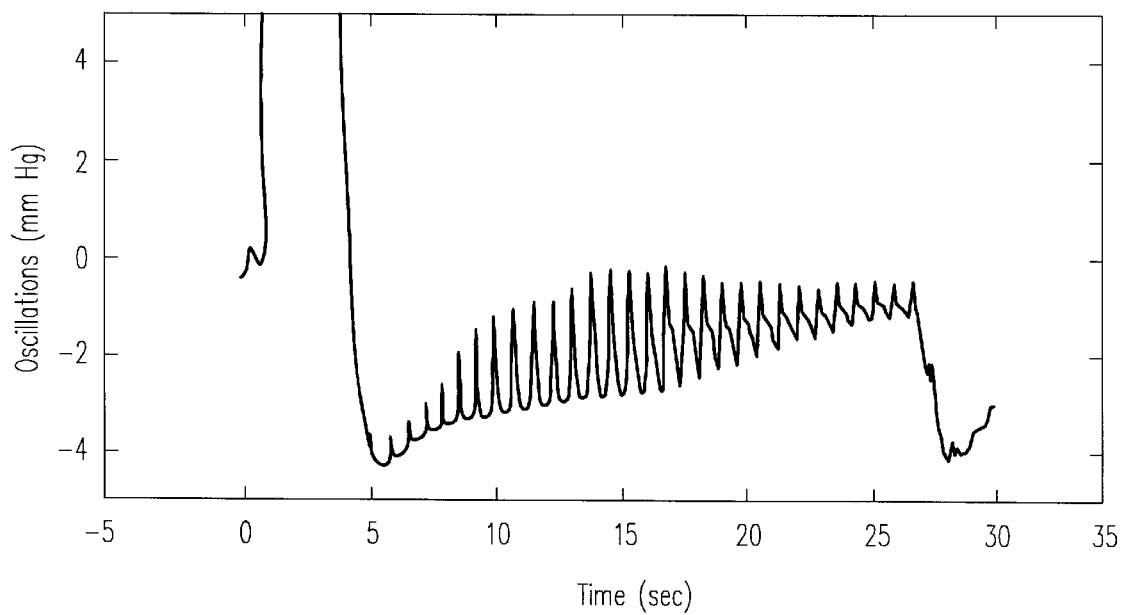
FIG. 2B illustrates the portion of the waveform of FIG. 2A having a frequency between 0.5 and 5 Hz.
Figure 3:
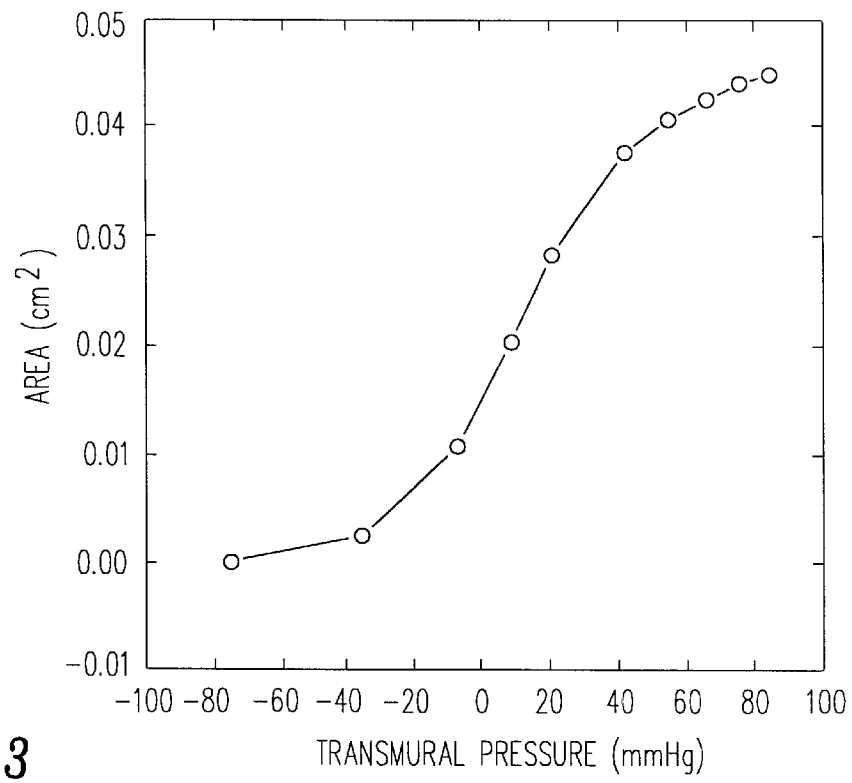
FIG. 3 illustrates the relationship between artery lumen area and transmural pressure.
Figure 4:
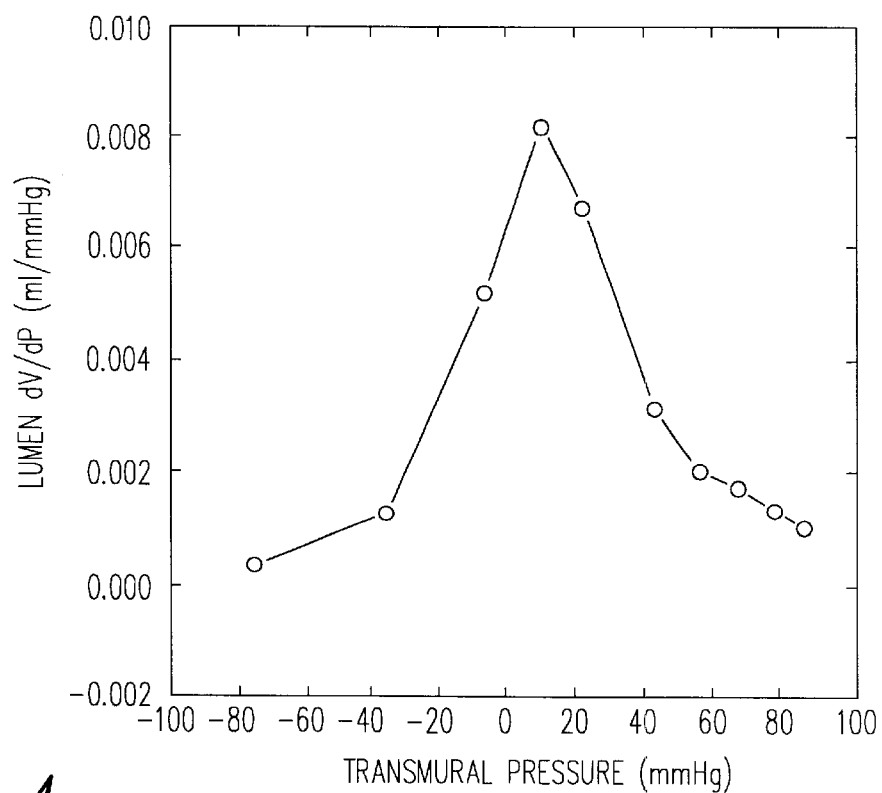
FIG. 4 illustrates the relationship between artery compliance and transmural pressure.
Figure 5:
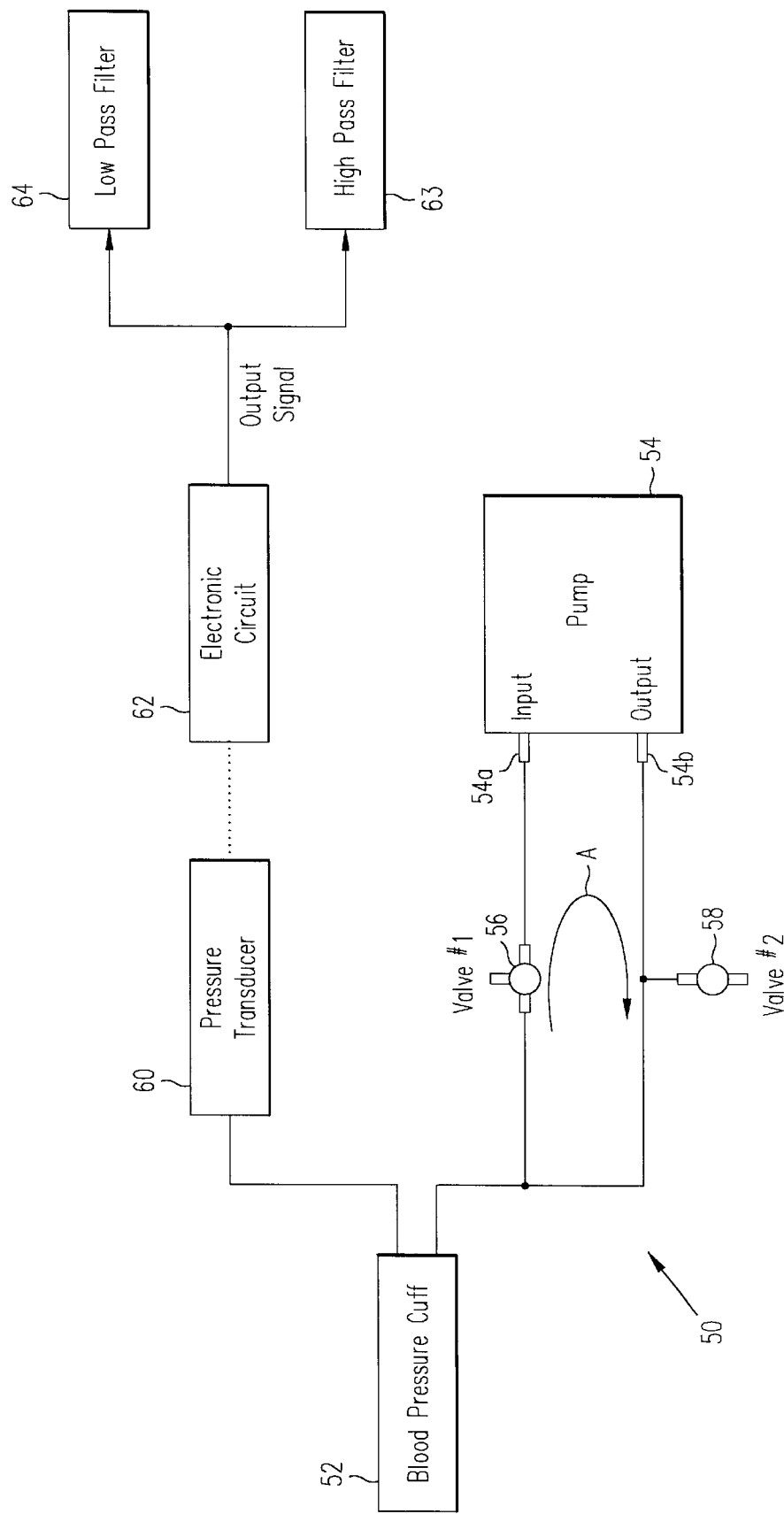
FIG. 5 illustrates Pilla's apparatus for measuring the lumen size of an artery with an occlusive cuff.
Figure 6:
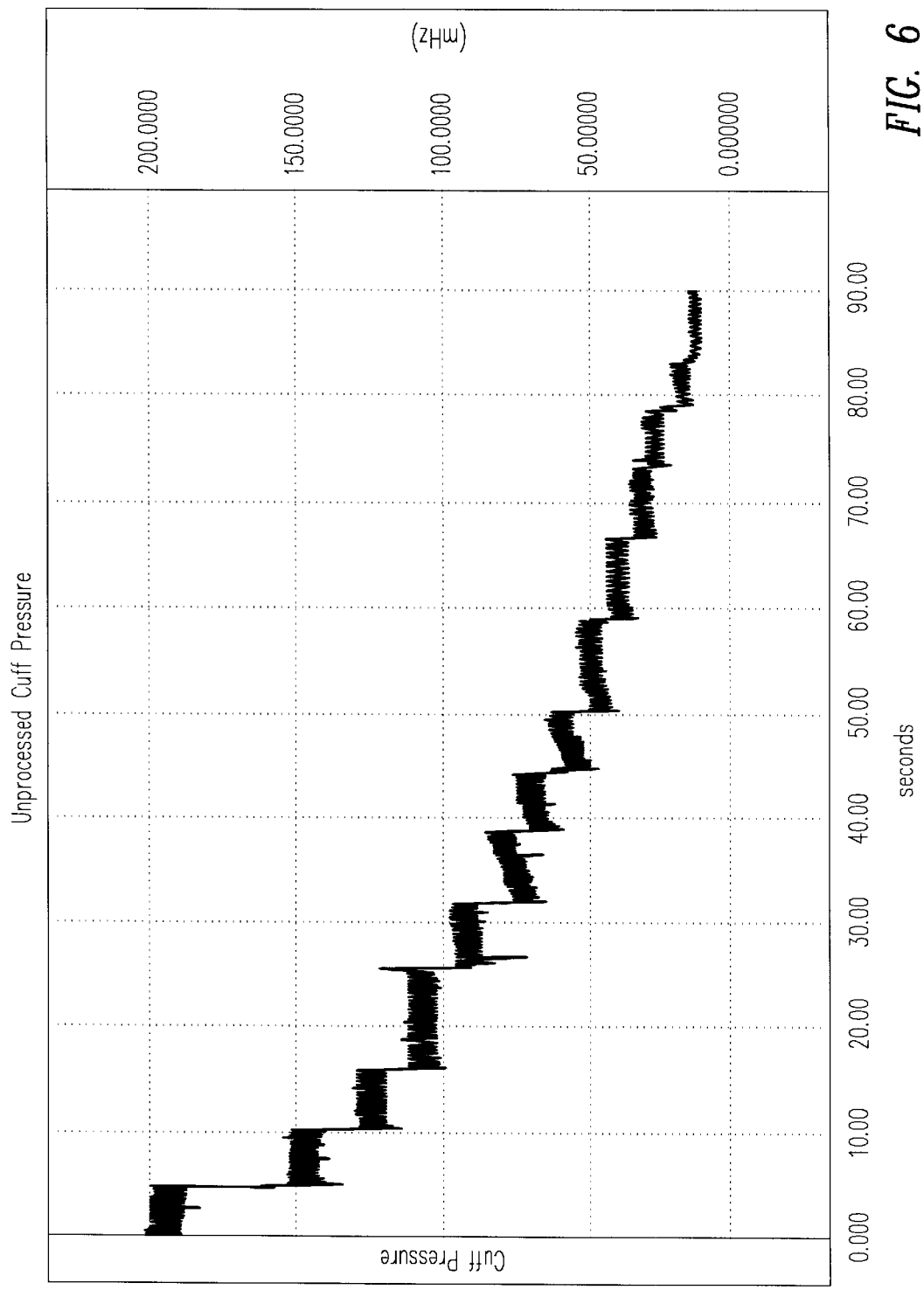
FIG. 6 illustrates a cuff pressure waveform provided by Pilla's apparatus.
Figure 6A:
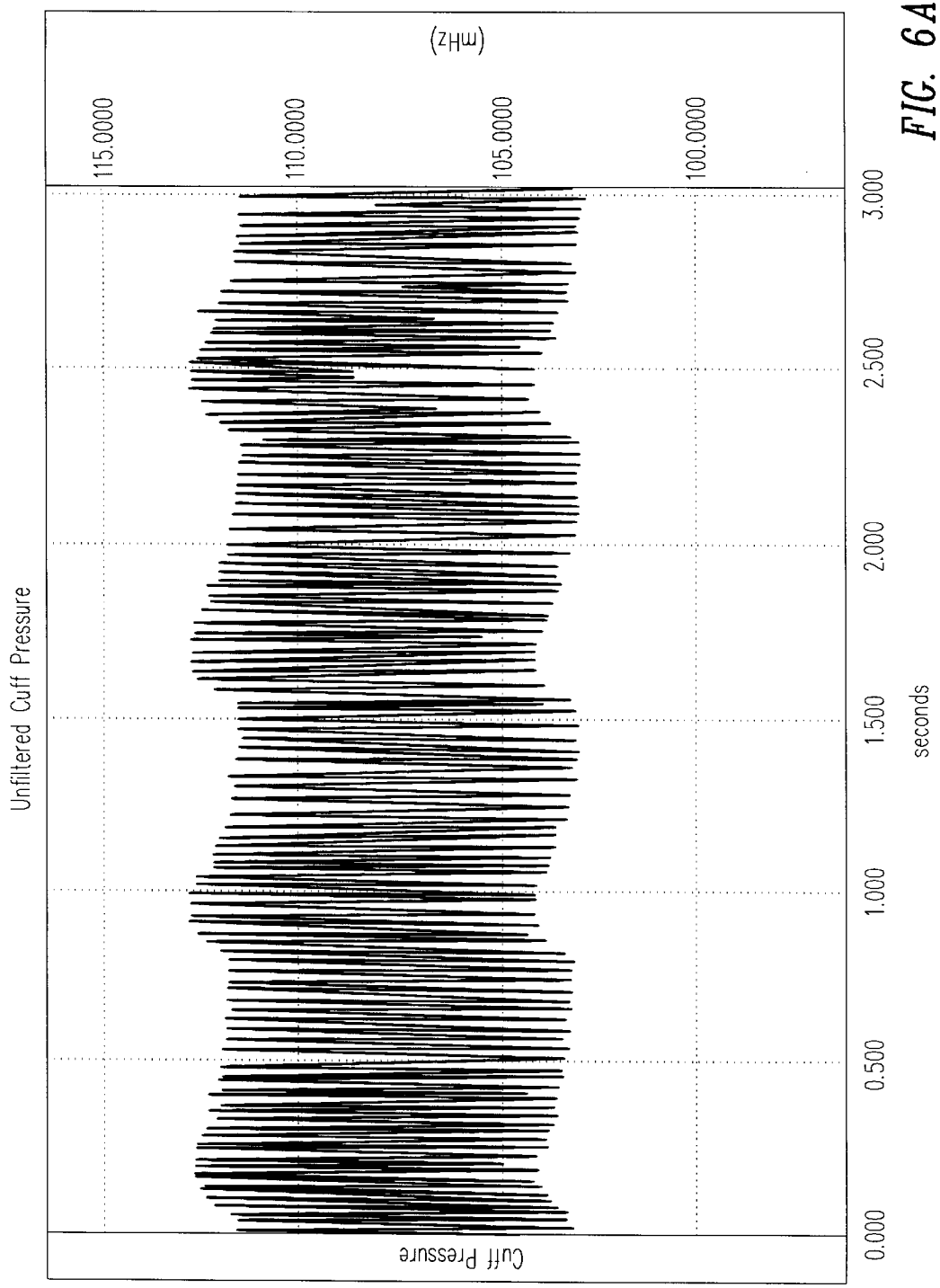
FIG. 6A is an amplified portion of the waveform of FIG. 6.
Figure 6B:
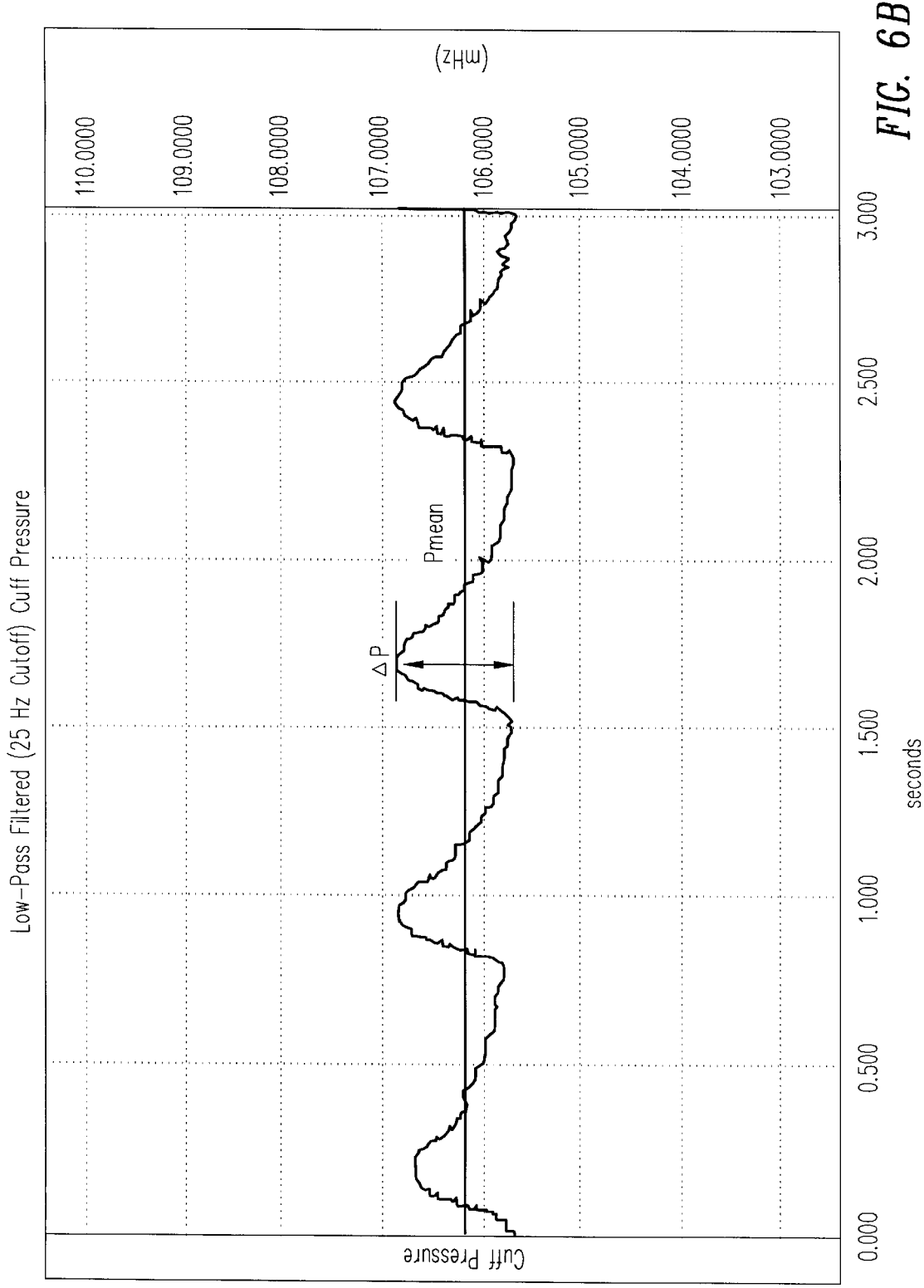
FIG. 6B illustrates the low frequency component of the signal of FIG. 6A.
Figure 6C:
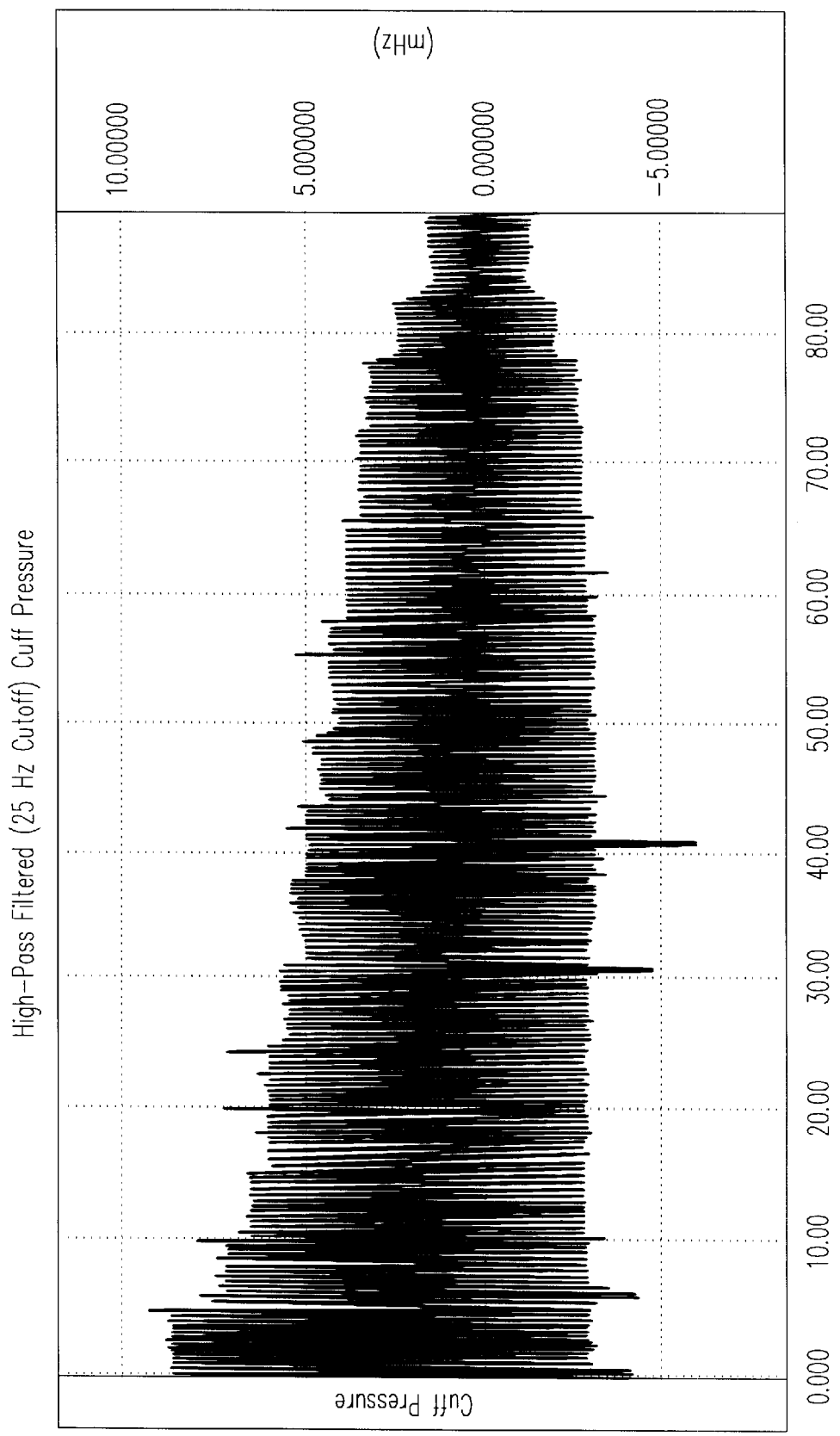
FIG. 6C illustrates the high frequency component of the signal of FIG. 6A.

Arterial volume compliance represents the amount that an artery expands as blood pressure increases. In other words, arterial volume compliance is the derivative of artery volume with respect to arterial pressure, and can be calculated as follows:

$$(dV/dP)_{artery} = dP_{artery\ at\ cuff} [(dV/dP)_{pump\ at\ cuff}/(SP-DP)]$$

where SP is the systolic pressure, and DP is the diastolic pressure. SP and DP are calculated as described above. $(dV/dP)_{pump\ at\ cuff}$ is the cuff compliance calculated as described above. $dP_{artery\ at\ cuff}$ is the amplitude of signal 120 provided by the low pass filter. Thus, all of the variables on the right side of the above equation are known, and therefore artery volume compliance is easily calculated. FIG. 4 illustrates the artery volume compliance of a typical artery, i.e. a graph of $dV/dP_{artery}$ vs. transmural pressure.

From the artery volume compliance data, one can calculate the artery area compliance $dA/dP_{artery}$ as follows:

$$dA/dP_{artery} = dV/dP_{artery}/(CL*CF)$$

where CL is the length of cuff 108, and CF is a correction factor. One should use the correction factor CF because the transmission of cuff pressure to the artery wall is not uniform along the entire artery length. There is an "edge effect" of a decreased transmission at the ends of the cuff that leads to the correction factor. Correction factor CL is determined by a method described below.

Figure 9:
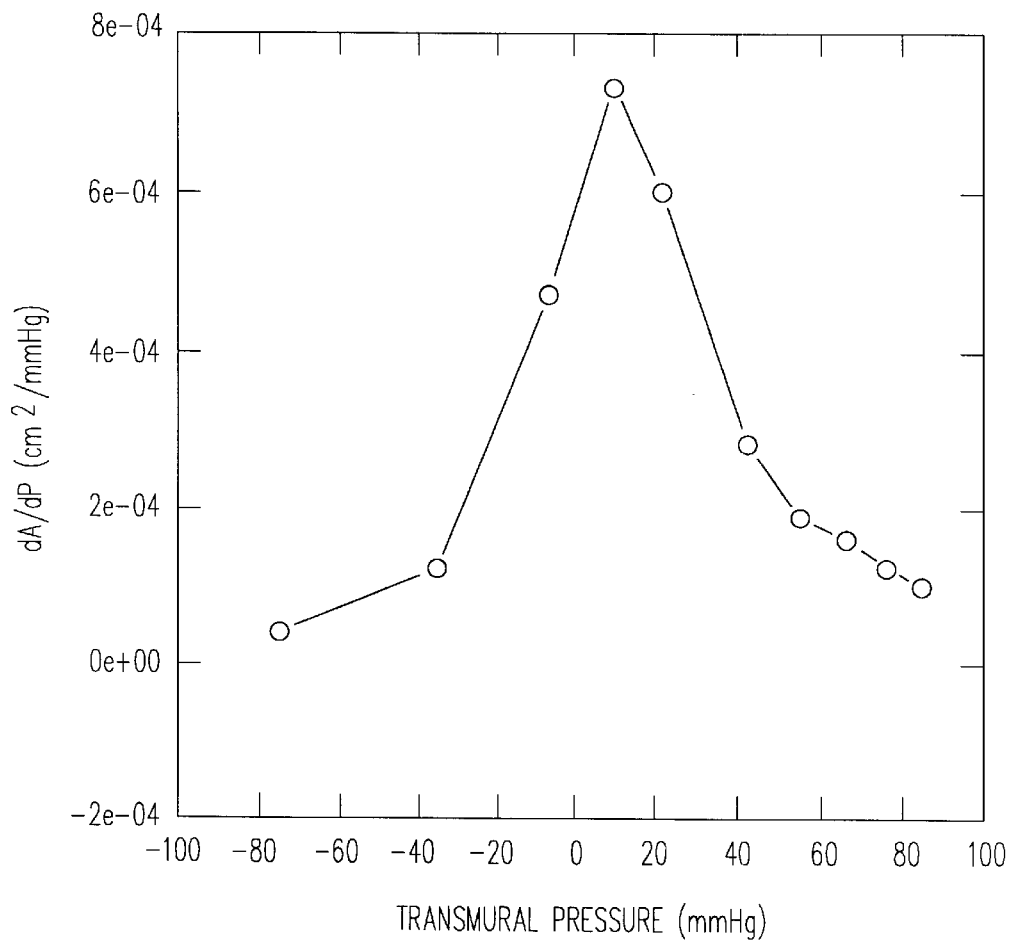
FIG. 9 shows an artery area compliance curve.

Once the term dA/dP artery is found, an arterial area compliance curve can be generated, e.g. as shown in FIG. 9. This curve shows the change in lumen area dA/dP as a function of transmural pressure.

Calculation of Lumen Area

Once one generates the artery area compliance curve (FIG. 9), one can calculate the artery lumen area by integrating to find the area under the artery area compliance curve. In other words, artery area A is calculated as follows:

$$A = \int (dA/dP) dP$$

This integration can be performed using numerical integration algorithms that are well known in the art. In one embodiment, an algorithm known as the trapezoidal rule is used to perform integration.

Calculation of Correction Factor CF

The correction factor CF for a given cuff can be obtained by using the cuff on a test subject, and measuring the test subject's artery lumen area by magnetic resonance imaging ("MRI") or other technique. The correction factor represents the ratio of the actual lumen area and the integral of $dV/dP_{artery}/CL$. In other words, $$CF = (\int dV/dP_{artery}) (CL * \text{actual artery lumen area}).$$

Thereafter, the correction factor CF for that cuff can be used on other test subjects without recalibrating the cuff against additional MRI data from those other test subjects. Of importance, providing the correction factor enhances the accuracy of our method.

Calculating Arterial Flow Waveform

The oscillometric data dP/dt from filter 120 is converted to volume flow of blood through the artery dV/dt by multiplying dP/dt by artery volume compliance $C = dV/dP$ as discussed in Whitt, et al., "Noninvasive Method for Measuring Flow from Oscillometric Data". However, as shown in FIG. 4, artery volume compliance changes with time at the differing cuff pressures. Therefore, the volume flow wave form is generated using the following equation:

$$dV/dt = C(t)(dP/dt) + P(t)(dC/dt)$$

One can compare the phase lag between blood flow and blood pressure. The phase lag is useful because it changes with different cardiovascular conditions. This is an additional variable with which to make clinical diagnoses.

While the above analysis can be performed using different kinds of circuitry and computers, in one embodiment we connect amplifier 111 to a Biopak Model UTM100. The UTM100 is an interface circuit for amplified signals. The UTM100 is connected to a Biopak Model MP100, which is an analog to digital conversion interface. The MP100 is connected to an NEC Versa 4050C Laptop Computer running Acknowledge Software.

Embodiment Using Multi-Bladder Cuff

Figure 10:
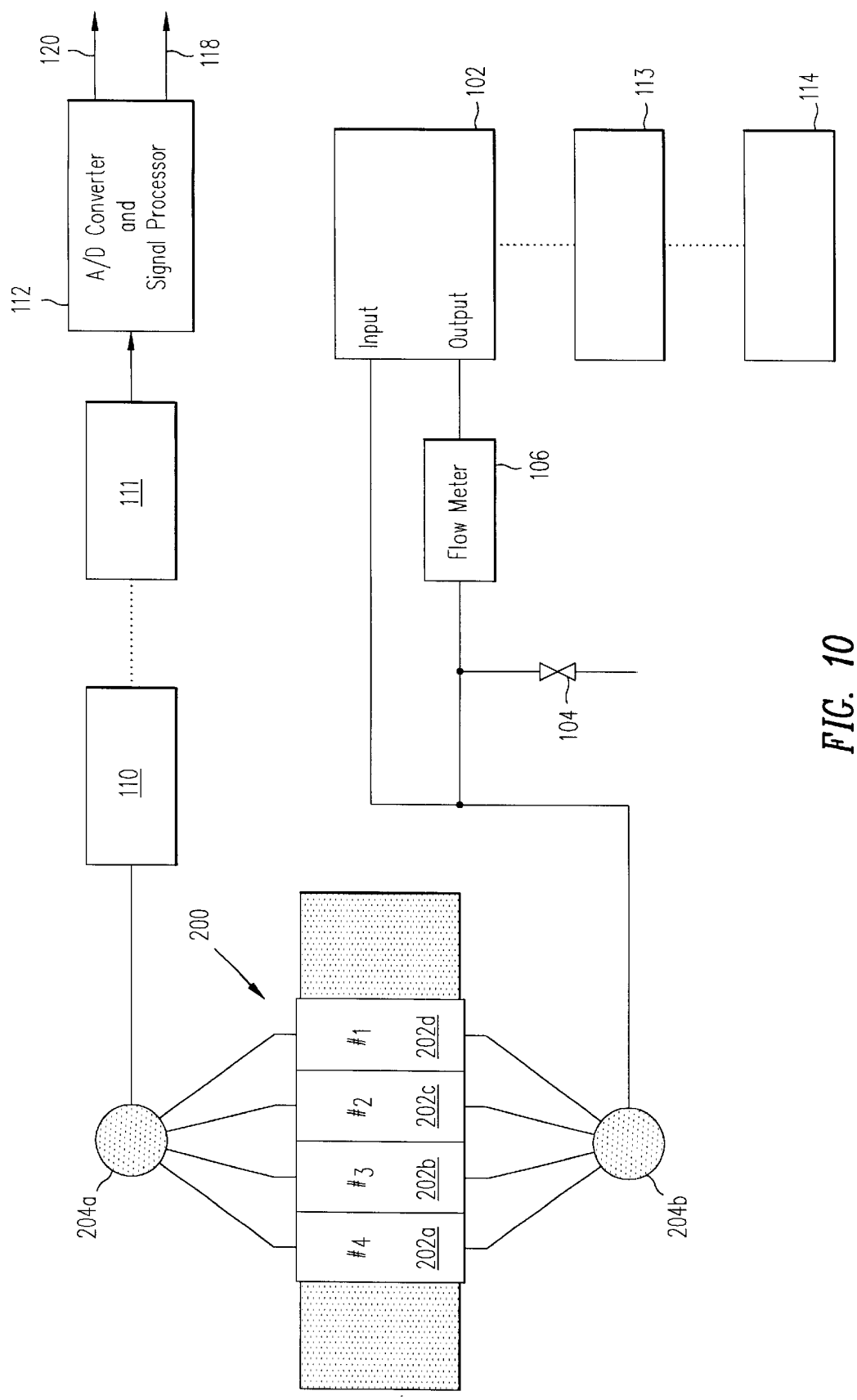
FIG. 10 illustrates an embodiment of our invention in which the cuff comprises multiple bladders.

Referring to FIG. 10, an alternative embodiment of our invention comprises a cuff 200 comprising four bladders 202a to 202d. (Although cuff 200 includes four bladders, other numbers of bladders can be used.) Bladders 202a to 202d are each connected to manifolds 204a and 204b. Manifold 204a selectively connects one of bladders 202a to 202d to transducer 110, and manifold 204b selectively connects that bladder to flow meter 106, valve 104 and pump 102.

Each of bladders 202a to 202d is individually inflated and deflated to obtain the compliance and artery cross section area in the same manner as the one bladder within cuff 108 of FIG. 7. Compliance and artery area for a series of segments of the brachial artery (each segment corresponding to one of bladders 202a to 202d) can therefore be obtained. Of importance, the location of a lesion in the brachial artery can be detected by locating a narrowing in the artery with the multi-bladder cuff.

In one embodiment, manifolds 204a and 204b can be connected to and controlled by the same circuitry used to calculate the various parameters discussed above.

In yet another embodiment, each bladder is associated with its own pressure transducer. A selected one of the pressure transducers are connected to an amplifier and A/D converter via a multiplexer.

While the invention has been described with respect to specific embodiments, those skilled in the art will appreciate that changes can be made in form and detail without departing from the spirit and scope of the invention. For example, cuff 108 can be placed around portions of the patient other than the patient's arm. Cuff 108 can be placed around the patient's leg to measure blood flow through and pressure within the femoral artery. Different types of motors, valves, pumps, flow meters, and computers can be used. The various calculations can be performed using analog or digital circuitry. Systolic and diastolic pressure can be obtained using the auscultatory method. Accordingly, all such modifications come within the invention.

What is claimed is:

1. A method for collecting data concerning a patient comprising the steps of:
   providing a cuff around a portion of a patient;
   pumping a fluid into said cuff;
   measuring the pressure variation in said cuff, a first portion of said pressure variation being a function of said fluid being pumped into said cuff, a second portion of said pressure variation being a function of the expansion and contraction of said portion of said patient caused by blood flowing through said portion of said patient;
   determining the volume of fluid pumped into said cuff per pump stroke;
   determining the relation between cuff volume and cuff pressure based on said determination of said volume of fluid pumped into said cuff per pump stroke; and
   determining the change in volume of said portion of said patient caused by blood flowing through said portion of said patient by monitoring said second portion of said pressure variation.

2. The method of claim 1 wherein said step of pumping a fluid is performed using a pump having a substantially flat volume vs. pressure curve in the pressure range used.

3. The method of claim 1 wherein said pump pumps at a frequency substantially greater than the heart rate of said patient.

4. The method of claim 1 further comprising the step of calculating the lumen area of an artery in said patient by determining the lumen area compliance of said artery across a range of transmural pressures and integrating said lumen area compliance with respect to said transmural pressure to arrive at the lumen area.

5. The method of claim 1 further comprising the step of calculating the blood flow rate through an artery of said patient based on said second portion of said pressure variation.

6. The method of claim 1 further comprising the step of calculating the phase lag between the pressure vs. time waveform and the blood volume flow vs. time waveform.

7. The method of claim 1 wherein said step of determining the volume is performed using a flow meter.

8. An apparatus comprising:
   a cuff for surrounding a portion of a patient;
   a pump for pumping a fluid into and out of said cuff;
   a flow meter coupled to said pump for measuring the volume of said fluid being pumped into and out of said cuff and determining a pump stroke volume for said pump;
   a transducer for measuring the pressure of the fluid in the cuff;
   filter circuitry for providing a measure of the change in cuff pressure caused by said pump and the change in cuff pressure caused by said patient's pulse; and
   circuitry for calculating a cuff compliance based on said pump stroke volume and said chance in cuff pressure caused by said pump and for calculating the change in the size of said portion of said patient caused by said patient's pulse based on said change in cuff pressure caused by said patient's pulse.

9. The apparatus of claim 8 wherein said circuitry calculates the chance in the area of the lumen of an artery of said patient caused by said patient's pulse.

10. An apparatus comprising:
    a cuff for surrounding a portion of a patient;
    a pump for pumping a fluid into and out of said cuff;
    a flow meter coupled to said pump for measuring the volume of said fluid being pumped into and out of said cuff and determining a pump stroke volume for said pump;
    a transducer for measuring the pressure of the fluid in the cuff;
    means for measuring the change in cuff pressure caused by said pump and the change in cuff pressure caused by said patient's pulse; and
    means for calculating a cuff compliance based on said pump stroke volume and said change in cuff pressure caused by said pump, and for calculating the change in the size of said portion of said patient caused by said patient's pulse based on said change in cuff pressure caused by said patient's pulse.

11. A method comprising the steps of
    providing a cuff including a plurality of bladders around a portion of a patient;
    inflating said bladders one at a time so that one of said bladders are in an inflated state;
    pumping a fluid in and out of each of said bladders when said bladders are inflated;
    measuring the pressure in said bladders when said bladders are inflated; and
    using said pressure to determine the area of the lumen of an artery extending through each bladder.

12. The method of claim 11 further comprising the steps of:
- measuring the volume of said fluid pumped in and out of said bladders;
- determining the bladder compliance based on said measure of the volume of said fluid and the measure of said pressure; and
- generating a measure of the change in cuff volume caused by a patient's pulse.

13. An apparatus comprising:

a cuff comprising a plurality of bladders therein;

a manifold for selectively connecting a selected one of said bladders to a pump, said pump pumping fluid in and out of said bladder; and a transducer for measuring the pressure at said selected bladder, said transducer being used to calculate lumen area of an artery.

14. An apparatus comprising:

a cuff comprising a plurality of bladders therein;

first means for selectively connecting a selected one of said bladders to a pump, said pump pumping fluid in and out of said bladder; and second means for measuring the pressure at said selected bladder, said second means calculating the lumen area of an artery.

* * * * *